United States Patent
Yoshida et al.

(10) Patent No.: US 6,914,119 B2
(45) Date of Patent: Jul. 5, 2005

(54) HEAT-RESISTANT POLYETHER, CURABLE POLYETHER, AND COATING LIQUID FOR FORMING A POLYETHER FILM

(75) Inventors: Yuji Yoshida, Edogawa-ku (JP); Mikio Takigawa, Tsukuba (JP); Naoya Satoh, Tsukuba (JP)

(73) Assignee: Sumitomo Chemical Company, Limited, Osaka (JP)

( * ) Notice: Subject to any disclaimer, the term of this patent is extended or adjusted under 35 U.S.C. 154(b) by 113 days.

(21) Appl. No.: 10/197,599

(22) Filed: Jul. 18, 2002

(65) Prior Publication Data

US 2003/0060591 A1 Mar. 27, 2003

(30) Foreign Application Priority Data

Jul. 31, 2001 (JP) ........................................ 2001-231222

(51) Int. Cl.⁷ .............................................. C08G 65/38
(52) U.S. Cl. ...................... 528/219; 528/218; 528/43; 528/29; 528/205
(58) Field of Search ................................ 528/205, 219, 528/29, 43, 218; 428/411.1, 446; 525/390, 391

(56) References Cited

U.S. PATENT DOCUMENTS

| | | | |
|---|---|---|---|
| H521 H | * | 9/1988 | Fan .............................. 525/391 |
| 5,874,516 A | | 2/1999 | Burgoyne et al. |
| 6,124,421 A | | 9/2000 | Lau et al. |
| 6,303,733 B1 | | 10/2001 | Lau et al. |
| 6,388,044 B1 | | 5/2002 | Yoshida et al. |

FOREIGN PATENT DOCUMENTS

| EP | 106023 | * | 4/1984 |
|---|---|---|---|
| JP | 2001-151884 A | | 6/2001 |
| JP | 2002-20482 A | | 1/2002 |

* cited by examiner

*Primary Examiner*—Margaret G. Moore
(74) *Attorney, Agent, or Firm*—Sughrue Mion, PLLC

(57) ABSTRACT

A heat-resistant polyether having a heat resistance to a temperature of 300° C. or higher, sufficient solubility in organic solvents, low water absorption and high adhesion to substrates is provided by a heat-resistant polyether including a repeating unit represented by the formula (1) and having a polystyrene-converted weight-average molecular weight determined by GPC of not less than 1000 and not more than 50000:

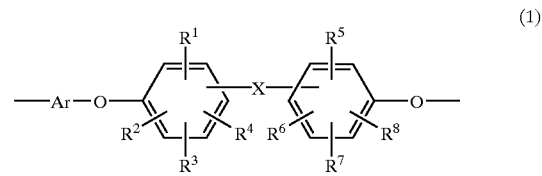

(1)

wherein Ar represents a bivalent organic group having an aromatic ring; $R^1$ to $R^8$ each independently represent a hydrogen atom or an aryl group which may be substituted; and when at least one of $R^1$ to $R^8$ is an aryl group which may be substituted, X represents a direct bond or a hydrocarbon group having 1 to 20 carbon atoms, while when all of $R^1$ to $R^8$ are hydrogen atoms, X is represented by the formula (2):

$$-CR^9(R^{10})-\qquad(2)$$

wherein $R^9$ and $R^{10}$ each independently represent an aryl group which may be substituted.

16 Claims, No Drawings

HEAT-RESISTANT POLYETHER, CURABLE POLYETHER, AND COATING LIQUID FOR FORMING A POLYETHER FILM

FIELD OF THE INVENTION

The present invention relates to a heat-resistant polyether, a curable polyether, a polyether film comprising the heat-resistant polyether or the curable polyether, a coating liquid containing the heat-resistant polyether or the curable polyether for forming a polyether film, an insulating film obtained from the coating liquid, and an electronic device having the insulating film.

BACKGROUND OF THE INVENTION

Insulating films and protective films for use in electronic devices such as ICs, LSIs and liquid crystal devices are required to have a heat resistance to a temperature of 300° C. or higher because temperature sometimes rise up higher during the process for manufacturing device. While ceramic-type films such as Spin On Glass (SOG) films have been conventionally used for such insulating films and protective films, use of organic polymers has been developed in recent years from the viewpoints of further improvements in insulating property and lowering of dielectric.

Polybenzimidazole and polypyromellitimide, for example, are excellent in heat resistance but are soluble only in strong acids such as concentrated sulfuric acid and hence cannot be used as protective films for plastics and metals.

Polyimides have high water absorption property and hence have a problem that the strength of adhesion to substrates week.

Accordingly, it is an object of the present invention to provide a heat-resistant polyether having a heat resistance to a temperature of 300° C. or higher, sufficient solubility in solvent, low water absorption and high adhesion to substrates such as silicone wafer.

SUMMARY OF THE INVENTION

The inventors of the present invention have found that a polyether having a repeating unit represented by the formula (1) and a weight-average molecular weight converted into molecular weight of polystyrene determined by GPC of from 1000 to 50000 has a heat resistance to a temperature of 300° C. or higher, sufficient solubility in solvents, low water absorption and high adhesion to substrates, and have completed the present invention.

That is, the present invention provides a heat-resistant polyether comprising a repeating unit represented by the formula (1) and having a weight-average molecular weight converted into molecular weight of polystyrene determined by GPC of from 1000 to 50000:

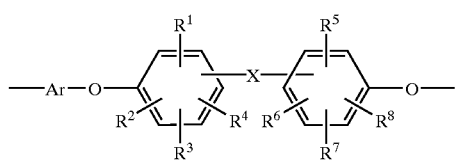

(1)

wherein Ar represents a bivalent organic group having an aromatic ring; $R^1$ to $R^8$ each independently represent a hydrogen atom or an aryl group which may be substituted; and when at least one of $R^1$ to $R^8$ is an aryl group which may be substituted, X represents a direct bond or a hydrocarbon group having 1 to 20 carbon atoms, while when all of $R^1$ to $R^8$ are hydrogen atoms, X is represented by the formula (2):

$$-CR^9(R^{10})- \qquad (2)$$

wherein $R^9$ and $R^{10}$ each independently represent an aryl group which may be substituted.

The present invention also provides a curable polyether comprising a heat-resistant polyether as described above which has further a functional group capable of crosslinking reaction.

Further, the present invention provides a polyether film comprising a heat-resistant polyether as described above or a curable polyether as described above, a coating liquid comprising one of these polyethers and an organic solvent for forming a polyether film, and an insulating film obtained from the coating liquid, as well as an electronic device having such an insulating film.

DETAILED DESCRIPTION OF THE INVENTION

A polyether according to the present invention is a heat-resistant polyether comprising a repeating unit represented by the formula (1) as shown above and having a weight-average molecular weight converted into molecular weight of polystyrene determined by GPC (hereinafter, sometimes referred as the polystyrene-converted weight-average molecular weight) of from 1000 to 50000.

If the polystyrene-converted weight-average molecular weight is less than 1000, the heat resistance of the polyether is not sufficient, while if it is more than 50000, a polyether film-forming coating liquid comprising the polyether has an increased viscosity and hence deteriorates coating property.

Ar in the formula (1) represents a bivalent organic group having one or plural aromatic rings. If the organic group has plural aromatic rings, these aromatic rings may be bonded to each other either directly or through a hydrocarbon group having 1 to 10 carbon atoms, ether group, carbonyl group, carboxyoxy group (—COO— or —OCO—), or sulfonyl group (—SO$_2$—).

Examples of such aromatic rings include benzene ring and naphthalene ring. An alkyl group may be bonded to each of these rings.

Preferably, Ar is selected from the following group (A) consisting of bivalent organic groups. These are easy to produce industrially because their dihalides derivatives are commercially available.

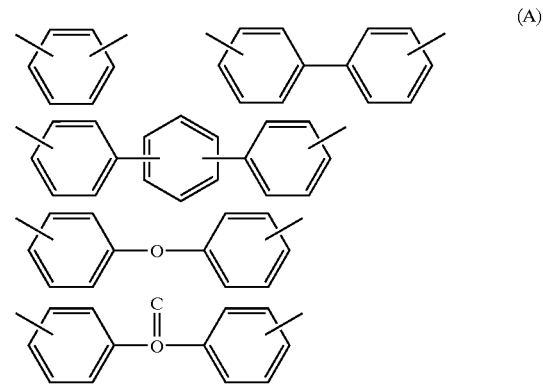

(A)

When at least one of $R^1$ to $R^8$ is an aryl group which may be substituted, X in the formula (1) is a direct bond or a hydrocarbon group having 1 to 20 carbon atoms. The expression "X is a direct bond", as used herein, means that benzene rings are bonded to each other directly in the formula (1). There is no particular limitation on the bonding position. Since preferable X has a structure free from any hetero-atom from the viewpoints of insulating property and low water absorption, the hydrocarbon group having 1 to 20 carbon atoms is preferable and the hydrocarbon group selected from the following group (B) consisting of bivalent organic groups is more preferable:

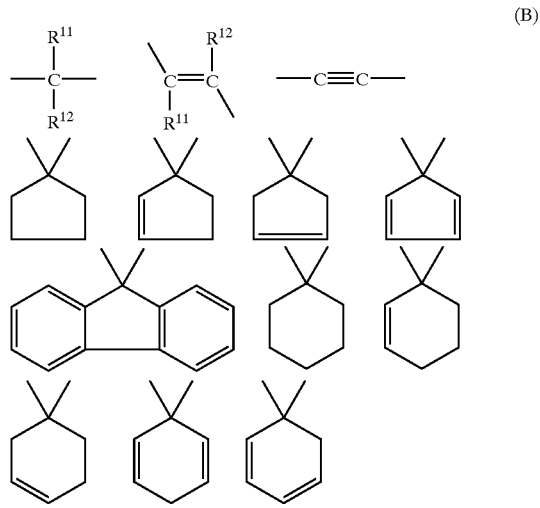
(B)

wherein $R^{11}$ and $R^{12}$ each represent an aryl group which may be substituted. Examples of such aryl groups which may be substituted for use as $R^{11}$ and $R^{12}$ include those aryl groups same as exemplified for $R^1$ and $R^8$ as shown below.

When all of $R^1$ to $R^8$ in the formula (1) are hydrogen atoms, X is represented by the formula (2):

$$-CR^9(R^{10})-\quad (2)$$

wherein $R^9$ and $R^{10}$ each independently represent an aryl group which may be substituted.

$R^1$ to $R^8$ in the formula (1) each independently represent a hydrogen atom or an aryl group which may be substituted.

Examples of such aryl groups which may be substituted include a group having an aromatic ring such as benzene ring or naphthalene ring. An alkyl group may be bonded to such an aromatic ring. Such an aryl group may have one or plural aromatic rings. When the aryl group has plural aromatic rings, the rings may be bonded to each other either directly or through an alkylene group having 1 to 3 carbon atoms, alkenylene group having 2 or 3 carbon atoms, alkynylene group having 2 or 3 carbon atoms, ether group, carbonyl group, carboxyoxy group, or sulfonyl group.

Specific examples of $R^1$ to $R^8$ include phenyl group, naphthyl group, biphenyl group, terphenyl group, toluyl group, ethylphenyl group, propylphenyl group, dimethylphenyl group, diphenylphenyl group, dimethylnaphthyl group, ethylnaphthyl group, propylnaphthyl group, methylbiphenyl group, dimethylbiphenyl group, trimethylbiphenyl group, methylterphenyl group, dimethylterphenyl group, trimethylterphenyl group, tetramethylterphenyl group, phenyloxyphenyl group, toluyloxyphenyl group, dimethylphenyloxyphenyl group, trimethylphenyloxyphenyl group, diphenoxyphenyl group, phenylketophenyl group, methylphenylketophenyl group, dimethylphenylketophenyl group, benzylphenyl group, phenylethylphenyl group, phenylpropylphenyl group, phenylbutylphenyl group, phenylhexylphenyl group, phenylethynylphenyl group, phenylpropylphenyl group, phenylbutenylphenyl group, phenylethenylphenyl group, phenylpropynylphenyl group, and phenylsulfonylphenyl group.

$R^9$ and $R^{10}$ in the formula (2) each represent an aryl group which may be substituted. Examples of such aryl groups include those aryl groups same as exemplified for $R^1$ to $R^8$.

More preferable aryl groups which may be substituted for use as $R^1$ to $R^{10}$ are those having one to three aromatic rings. In the case of an aryl group having two or more aromatic rings, it is preferred that a carbon atom directly bonded to such aromatic rings as a combining group has no hydrogen atom. If a carbon atom directly bonded to aromatic rings has any hydrogen atom, the resulting polyether may be deteriorated by autoxidation, so that decomposition of the polyether is likely to be facilitated under a heat treatment in the presence of oxygen.

Among such aryl groups which may be substituted, particularly preferable are those aryl groups having two or less aromatic rings of the following group (C):

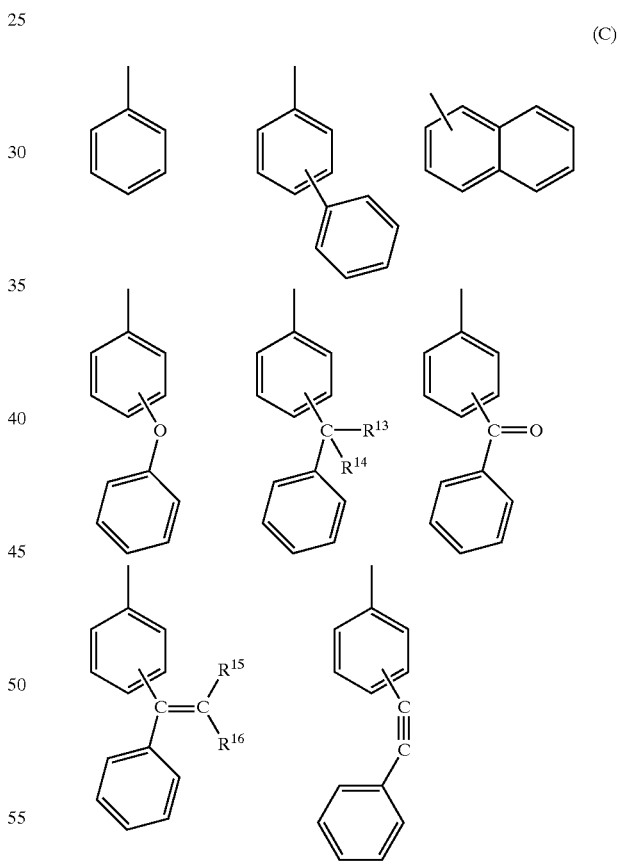
(C)

wherein $R^{13}$ to $R^{16}$ each independently represent an alkyl group having 1 to 3 carbon atoms.

If the aryl group has three or more aromatic rings, the reactivity of group Y, which is a reactive site of a monomer represented by the following formula (4) or (5) for the preparation of the polyether, is lowered due to steric hindrance, with the result that the time period required for polymerization tends to become longer.

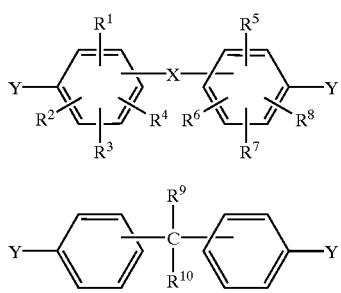

wherein $R^1$ to $R^8$ and X each are the same as in the formula (1); $R^9$ to $R^{10}$ each are the same as in the formula (2); and Y represents a hydroxyl group, trimethylsilyloxy group, fluorine atom, chlorine atom, bromine atom, iodine atom, mesyl group, or tosyl group.

In view of making polymerization time period shorter, it is particularly preferred that at least one of $R^1$ to $R^8$ in the formula (1) or at least one of $R^9$ and $R^{10}$ in the formula (2) be a phenyl group. Monomers each having a phenyl group are those of the following group (E) for example. These monomers are preferable because they are commercially available.

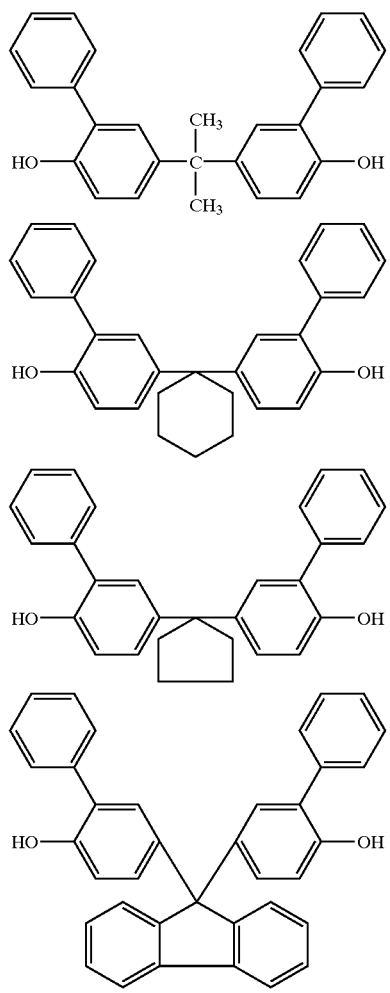

The heat-resistant polyether of the present invention, for example, may be obtained through condensation polymerization of the monomer represented by the formula (4) or (5) above. The monomer represented by the formula (4) or (5) may be a commercially-available product, for example, a bisphenol monomer having a hydroxyl group as Y or may be synthesized from a corresponding phenol and a ketone, aldehyde or the like having the group X with use of a strong acid such as sulfuric acid or trifluoroacetic acid as a catalyst. If the bisphenol monomer is reacted with tosyl chloride or mesyl chloride, for example, a monomer having a tosyl or mesyl group as Y can be synthesized. On the other hand, a monomer having a halogen as Y can be synthesized by directly halogenating a corresponding aromatic compound with bromine/bromine chloride or iodine/silver sulfate for example.

The intended polymer can be prepared by condensation-polymerizing a hydroxyl group represented by the formula (4) or (5), which is thus synthesized by the method described above, with a halogen, tosyl group or mesyl group via inter- or intra-molecular condensation. The condensation polymerization may be conducted under usual conditions. For example, the condensation polymerization is conducted under the conditions:

Catalyst: alkaline catalyst,
co-catalyst: copper salt such as copper chloride or copper bromide, or copper-pyridine complex,
condensation-polymerization temperature: 80–200° C.,
condensation-polymerization time period: 0.5–30 hours.

Next, description will be made of the curable polyether of the present invention. The curable polyether comprises a heat-resistant polyether having the repeating unit represented by the formula (1) further having a functional group in a molecular chain thereof, the functional group being capable of crosslinking reaction. The "crosslinking reaction", as used herein, means a reaction causing new linkage to occur between two or more functional groups of the polymer. The crosslinking reaction is caused by heating or UV irradiation. Examples of such crosslinking reactions include radical addition reaction causing carbon-carbon unsaturated groups to be coupled to each other, Diels-Alder reaction between a conjugated diene and a carbon-carbon unsaturated group, 1,3-dipolar addition reaction between an azido group, a nitrile oxide group and a carbon-carbon unsaturated group, and reaction to produce siloxane through dehydrocondensation between silanol groups.

The number of such functional groups per one repeating unit represented by the formula (1) is about 0.01 to about 2, preferably 0.05 to 1.5.

In general, the functional group capable of crosslinking reaction may be introduced into the heat-resistant polyether that has been prepared in advance.

The functional group is preferably a functional group having a carbon atom directly bonded to an aromatic ring and no hydrogen atom from the viewpoint of heat resistance of the obtained polymer. Specifically, such preferable functional groups include those functional groups selected form the following group (D) or represented by the formula (3).

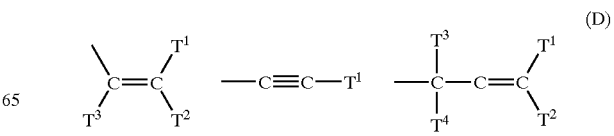

-continued

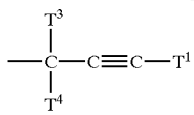

wherein T¹ and T² each represent a hydrogen atom, an alkyl group having 1 to 3 carbon atoms, or an aryl group which may be substituted; and T³ and T⁴ each represent an alkyl group having 1 to 3 carbon atoms or an aryl group which may be substituted.

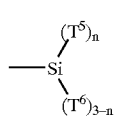
(3)

wherein T⁵ represents an alkenyl group having 2 or 3 carbon atoms or an alkynyl group having 2 or 3 carbon atoms; T⁶ represents an alkyl group having 1 to 3 carbon atoms or an aryl group which may be substituted; n is 1, 2 or 3; when n is 2 or 3, T⁵'s may be the same or different, while when n is 1, T⁶'s may be the same or different; and T¹ to T⁶ are the same or different with each other.

Examples of functional groups selected from the group (D) include vinyl group, allyl group, propenyl group, isopropenyl group, butenyl group, hexenyl group, 2-methyl-2-propenyl group, 2,2-diphenylvinyl group, styryl group, naphthalenevinylene group, toluylenevinylene group, ethynyl group, propargyl group, propynyl group, butynyl group, hexynyl group, phenylacetylene group, and naphthylacetylene group.

Examples of functional groups represented by the formula (3) include vinyldimethylsilyl group, vinyldiethylsilyl group, vinyldipropylsilyl group, vinyldiphenylsilyl group, vinyldinaphthylsilyl group, vinylmethylnaphthylsilyl group, vinyldimethylsilyl group, vinyldiethylsilyl group, vinyldipropylsilyl group, vinyldiphenylsilyl group, divinylmethylsilyl group, divinylethylsilyl group, divinylpropylsilyl group, divinylphenylsilyl group, allyldimethylsilyl group, allyldiethylsilyl group, allyldipropylsilyl group, allyldiphenylsilyl group, allyldinaphthylsilyl group, allylmethylnaphthylsilyl group, allyldimethylsilyl group, allyldiethylsilyl group, allyldipropylsilyl group, allyldiphenylsilyl group, diallylmethylsilyl group, diallylethylsilyl group, diallylpropylsilyl group, diallylphenylsilyl group, butenyldimethylsilyl group, butenyldiethylsilyl group, pentenyldimethylsilyl group, pentenyldiethylsilyl group, octenyldimethylsilyl group, decanyldimethylsilyl group, trivinylsilyl group, triallylsilyl group, tributenylsilyl group, trioctenylsilyl group, vinyldiallylsilyl group, divinylallysilyl group, and divinyloctenylsilyl group.

The functional group represented by the formula (3) is preferable as the functional group capable of crosslinking reaction by heating, since it may be easily introduced into the heat-resistant polyether of the present invention on the grounds that: it is easy to obtain halogenated silane as a precursor of the functional group; and the reactivity of its silicon-halogen bond is high enough.

Among them, trivinylsilyl group is suitably used because a curable polyether obtained by introduction of this group has so high crosslinking reactivity that crosslinking is achieved at a low temperature.

In the case of forming a film by drying a coating liquid as will be described later, if the coating liquid comprises the curable polyether, the curable polyether may have a crosslinked structure through heating or UV irradiation performed in the film-forming process. The curable polyether having a crosslinked structure is a curable polyether having a three-dimensional network structure resulting from such crosslinking reaction. Either a part or all of the functional groups capable of crosslinking reaction may be crosslinked.

The coating liquid for forming a polyether film according to the present invention comprises the aforementioned heat-resistant polyether or the aforementioned curable polyether, and an organic solvent.

Examples of organic solvents for use in the coating liquid include alcohols such as methanol, ethanol, isopropyl alcohol, butanol, t-butyl alcohol, methoxymethanol, 2-methoxyethanol, 2-ethoxyethanol, 4-ethoxybutanol, cyclohexyl alcohol, and furfuryl alcohol; esters such as ethyl acetate, propyl acetate, n-butyl acetate, isobutyl acetate, propylene glycol monomethyl ether acetate, methyl propionate, ethyl propionate, methyl butyrate, ethyl butyrate, ethyl lactate, and propyl lactate; ketones such as 2-pentanone, 3-pentanone, 2-hexanone, 3-hexanone, methyl isobutyl ketone, 2-heptanone, 3-heptanone, acetylacetone, cyclopentanone, and cyclohexanone; ethers such as diethyl ether, dibutyl ether, tetrahydrofuran, tetrahydropyran, and methyltetrahyropyran; phenol ethers such as anisole, phenetole, veratrole, diphenyl ether; carbonates such as dimethyl carbonate and diethyl carbonate; and aromatic hydrocarbons such as toluene, xylene, and mesitylene. These may be used either alone or as mixtures of at least two of them.

The concentration of polyether in the polyether film-forming coating liquid is preferably from 5% to 40% by weight, more preferably from 10% to 20% by weight. If the concentration of polyether is less than 5% by weight, the spin coating process, if employed for coating, may require application of the coating liquid several times to attain a desired film thickness because thickness formed by this process is thin. On the other hand, if the polyether concentration is more than 40% by weight, the feeding of the coating liquid or the like during coating may become troublesome due to an increase in the viscosity of the coating liquid.

The polyether film-forming coating liquid of the present invention may include additives such as a surface-active agent and an antioxidant unless they deteriorate the chemical resistance of the coating liquid and the strength of a film formed from the coating liquid. In the case where the functional group capable of crosslinking reaction has an unsaturated group, a catalyst, such as a peroxide or an azo compound, mat be added to the coating liquid because the crosslinking reaction may occur at lower temperature by adding these catalyst.

The polyether film-forming coating liquid of the present invention is capable of forming a heat-resistant polyether film or a curable polyether film through a process including: for example, applying the coating liquid onto an electronic device by spin coating or dipping; removing the solvent; and allowing the coating liquid thus applied to cure through a heat treatment, irradiation of light or other method if necessary.

The polyether film-forming coating liquid of the present invention is capable of coating substrates of metal, ceramic, plastic or glass thereby imparting them with a heat resistance.

A heat-resistant or curable polyether film formed from the polyether film-forming coating liquid can be used as an insulating film or protective film for use in an electronic device. The polyether film of the present invention can be particularly suitably used as an insulating film for maintaining insulation between adjacent interconnecting metal wires of aluminum, copper or an alloy thereof. Alternatively, since the polyether film has low water absorption, it may be used also as a protective film for protecting an electronic device in which a circuit has already been formed against intrusion of water or metal ion from the external environment.

When the polyether film is to be used as an insulating film, the film may be rendered the dielectric constant lower by making the film porous by any method. Since lowering the dielectric constant of the polyether film by making the film porous is due to a change in the physical form but not in the chemical structure of the polyether film, chemical characteristics, such as a high heat resistance, of the film are maintained.

EXAMPLE

Hereinafter, the present invention will be described more specifically by way of examples, which should not be construed to limit the scope of the present invention.

Example 1

A four neck flask of 500 ml was charged with 34 g (0.08 mol) of 1,1-bis(4-hydroxy-3-phenylphenyl)cyclohexylidene, 6.4 g of caustic soda, 110 g of benzophenone and 60 g of toluene to allow reflux dehydration to proceed. After completion of dehydration, 25 g (0.08 mol) of dibromobiphenyl was added into the flask. Further, a mixed liquid of cuprous chloride-pyridine was added into the flask as a catalyst, and the mixture in the flask was allowed to react at an internal temperature of from 170 to 190° C. for 8 hours. After having been cooled to room temperature, the reaction liquid was diluted with tetrahydrofuran, and the diluted liquid was added to a large quantity of a mixed liquid of methanol-acetic acid to precipitate a reaction product. The precipitated crystal was filtered, washed with a large quantity of methanol and then dried under reduced pressure, to give a polyether. The polystyrene-converted weight-average molecular weight of this polyether determined by GPC (with HLC8120 manufactured by TOSOH CO., column: TSKgel SuperH 3000, developer: tetrahydrofuran at a flow rate of 0.8 ml/min) was 4600. This polyether is referred to as resin A. The thermal decomposition temperature of resin A determined by thermogravimetric analysis (with DTA-60 manufactured by SHIMADZU CO., representation with 0.1 wt % reduction under a heat-up condition of 10° C./min) was 390° C.

Example 2

A four neck flask of 500 ml was charged with 30 g (0.080 mol) of 1,1-bis(4-hydroxy-3-phenylphenyl)isopropylidene, 6.4 g of caustic soda, 110 g of benzophenone and 60 g of toluene to allow reflux dehydration to proceed. After completion of dehydration, 25 g (0.08 mol) of dibromobiphenyl was added into the flask. Further, a mixed liquid of cuprous chloride-pyridine was added into the flask as a catalyst, and the mixture in the flask was allowed to react at an internal temperature of from 170 to 190° C. for 6 hours. After having been cooled to room temperature, the reaction liquid was diluted with tetrahydrofuran, and the diluted liquid was added to a large quantity of a mixed liquid of methanol-acetic acid to precipitate a reaction product. The precipitated crystal was filtered, washed with a large quantity of methanol and then dried under reduced pressure, to give a polyether. The polystyrene-converted weight-average molecular weight of this polyether was 4600. The polyether thus obtained is referred to as resin B. The thermal decomposition temperature of resin B determined by thermogravimetric analysis was 380° C.

Example 3

A four neck flask of 500 ml was charged with 28 g (0.080 mol) of bis(4-hydroxyphenyl)diphenylmethane, 6.4 g of caustic soda, 110 g of benzophenone and 60 g of toluene to allow reflux dehydration to proceed. After completion of dehydration, 25 g (0.080 mol) of dibromobiphenyl was added into the flask. Further, a mixed liquid of cuprous chloride-pyridine was added into the flask as a catalyst, and the mixture in the flask was allowed to react at an internal temperature of from 170 to 190° C. for 20 hours. After having been cooled to room temperature, the reaction liquid was diluted with tetrahydrofuran, and the diluted liquid was added to a large quantity of a mixed liquid of methanol-acetic acid to precipitate a reaction product. The precipitated crystal was filtered, washed with a large quantity of methanol and then dried under reduced pressure, to give a polyether. The polystyrene-converted weight-average molecular weight of this polyether was 3700. The polyether thus obtained is referred to as resin C. The thermal decomposition temperature of resin C determined by thermogravimetric analysis was 430° C.

Example 4

A four neck flask of 500 ml was charged with 28 g (0.056 mol) of 9,9-bis(4-hydroxy-3-phenylphenyl)fluorene, 6.6 g of caustic soda, 110 g of benzophenone and 60 g of toluene to allow reflux dehydration to proceed. After completion of dehydration, 17 g (0.056 mol) of dibromobiphenyl was added into the flask. Further, a mixed liquid of cuprous chloride-pyridine was added into the flask as a catalyst, and the mixture in the flask was allowed to proceed at an internal temperature of from 170 to 190° C. for 14 hours. After having been cooled to room temperature, the reaction liquid was diluted with tetrahydrofuran, and the diluted liquid was added to a large quantity of a mixed liquid of methanol-acetic acid to precipitate a reaction product. The precipitated crystal was filtered, washed with a large quantity of methanol and then dried under reduced pressure, to give a polyether. The polystyrene-converted weight-average molecular weight of this polyether was 1500. The polyether thus obtained is referred to as resin D. The thermal decomposition temperature of resin D determined by thermogravimetric analysis was 400° C.

Example 5

Into a four neck flask of 300 ml, the internal atmosphere of which had bee replaced with nitrogen, were put 10 g of the polyether resin obtained in EXAMPLE 1 as a raw material and 200 ml of tetrahydrofuran as a solvent, to cause the polyether resin to be dissolved in the solvent. After the internal temperature of the flask had been lowered to 5° C. or lower by cooling, the solution was admixed with 17 ml of n-butyllithium (in 1.6 Mn-hexane solution) and then stirred for one hour in a stream of nitrogen. Thereafter, 4.1 g of trivinylsilyl chloride was added dropwise to the resulting mixture in one hour, followed by continuous stirring at the same temperature for about one hour. Further, the internal temperature of the flask was raised to room temperature, and then the mixture was continuously stirred for one hour. After completion of the reaction, the reaction solution was charged into a large quantity of a mixed liquid of methanol-acetic acid to cause a high-molecular weight substance to precipitate, and the precipitated high-molecular weight substance was filtered and then washed with methanol and with water, to give a curable polyether. The polystyrene-converted weight-average molecular weight of this curable polyether determined by GPC was 5500. According to verification of the introduction of trivinylsilyl group by $^1$H-NMR, the number of trivinylsilyl groups introduced per one repeating unit was 0.7. The polyether thus obtained is referred to as resin E. The thermal decomposition temperature of resin E determined by thermogravimetric analysis was 480° C.

Example 6

Into a four neck flask of 300 ml, the internal atmosphere of which had bee replaced with nitrogen, were put 9.3 g of the polyether resin obtained in EXAMPLE 2 as a raw material and 190 ml of tetrahydrofuran as a solvent, to cause the polyether resin to be dissolved in the solvent. After the internal temperature of the flask had been lowered to 5° C. or lower by cooling, the solution was admixed with 17 ml of n-butyllithium (in 1.6 Mn-hexane solution) and then stirred for one hour in a stream of nitrogen. Thereafter, 4.1 g of trivinylsilyl chloride was added dropwise to the resulting mixture in one hour, followed by continuous stirring at the same temperature for about one hour. Further, the internal temperature of the flask was raised to room temperature, and then the mixture was continuously stirred for one hour. After completion of the reaction, the reaction solution was charged into a large quantity of a mixed liquid of methanol-acetic acid to cause a high-molecular weight substance to precipitate, and the precipitated high-molecular weight substance was filtered and then washed with methanol and with water, to give 8.7 g of a curable polyether. The polystyrene-converted weight-average molecular weight of this curable polyether determined by GPC was 9500. According to verification of the introduction of trivinylsilyl group by $^1$H-NMR, the number of trivinylsilyl groups introduced per one repeating unit was 1.2. The polyether thus obtained is referred to as resin F. The thermal decomposition temperature of resin F determined by thermogravimetric analysis was 480° C.

Example 7

Into a four neck flask of 300 ml, the internal atmosphere of which had been replaced with nitrogen, were put 3.0 g of the polyether resin obtained in EXAMPLE 3 as a raw material and 60 ml of tetrahydrofuran as a solvent, to cause the polyether resin to be dissolved in the solvent. After the internal temperature of the flask had been lowered to 5° C. or lower by cooling, the solution was admixed with 7.4 ml of n-butyllithium (in 1.6 Mn-hexane solution) and then stirred for one hour in a stream of nitrogen. Thereafter, 1.1 g of dimethylvinylsilyl chloride was added dropwise to the resulting mixture in one hour, followed by continuous stirring at the same temperature for about one hour. Further, the internal temperature of the flask was raised to room temperature, and then the mixture was continuously stirred for one hour. After completion of the reaction, the reaction solution was charged into a large quantity of a mixed liquid of methanol-acetic acid to cause a high-molecular weight substance to precipitate, and the precipitated high-molecular weight substance was filtered and then washed with methanol and with water, to give a curable polyether. The polystyrene-converted weight-average molecular weight of this curable polyether determined by GPC was 2500. According to verification of the introduction of dimethylvinylsilyl group by $^1$H-NMR, the number of dimethylvinylsilyl groups introduced per one repeating unit was 0.1. The polyether thus obtained is referred to as resin G. The thermal decomposition temperature of resin G determined by thermogravimetric analysis was 440° C.

Example 8

Into a four neck flask of 300 ml, the internal atmosphere of which had bee replaced with nitrogen, were put 14 g of the polyether resin obtained in EXAMPLE 4 as a raw material and 130 ml of tetrahydrofuran as a solvent, to cause the polyether resin to be dissolved in the solvent. After the internal temperature of the flask had been lowered to 5° C. or lower by cooling, the solution was admixed with 27 ml of n-butyllithium (in 1.6 Mn-hexane solution) and then stirred for one hour in a stream of nitrogen. Thereafter, 4.0 g of dimethylvinylsilyl chloride was added dropwise to the resulting mixture in one hour, followed by continuous stirring at the same temperature for about one hour. Further, the internal temperature of the flask was raised to room temperature, and then the mixture was continuously stirred for one hour. After completion of the reaction, the reaction solution was charged into a large quantity of a mixed liquid of methanol-acetic acid to cause a high-molecular weight substance to precipitate, and the precipitated high-molecular weight substance was filtered and then washed with methanol and with water, to give a curable polyether. The polystyrene-converted weight-average molecular weight of this curable polyether determined by GPC was 1600. According to verification of the introduction of dimethylvinylsilyl group by $^1$H-NMR, the number of dimethylvinylsilyl groups introduced per one repeating unit was 0.6. The polyether thus obtained is referred to as resin H. The thermal decomposition temperature of resin H determined by thermogravimetric analysis was 400° C.

Examples 9–11

Resins E F and H were each dissolved in anisole so that the resulting solution had a solid content of 15%, and the solution was filtered with a 0.1-$\mu$m PTFE filter. A 4-inch silicon wafer was coated with the solution thus obtained by spin coating at 2000 rpm, baked at 150° C. for one minute, and then heat-treated at 400° C. for 30 minutes in a nitrogen atmosphere. The thickness of the resulting film was measured using an optical thicknessmeter (NANOSPEC 210 manufactured by NANOMETRIC CO.), while the relative dielectric constant of the film was determined by C-V measurement (with SSM495 model manufactured by SSM CO.) at an operating frequency of 1 MHz according to the mercury probe method. Further, the adhesion of the film was determined by the Sebastian test. The results are shown in Table 1.

TABLE 1

| Example | Resin | Relative Dielectric Constant | Adhesion |
| --- | --- | --- | --- |
| 9 | E | 2.8 | >70 |
| 10 | F | 2.8 | >70 |
| 11 | H | 2.8 | >70 |

Examples 12–14

Resin D was dissolved in 2-heptanone so that the resulting solution had a solid content of 15%, and the solution was filtered with a 0.1-$\mu$m PTFE filter. A 4-inch silicon wafer was coated with the solution thus obtained by spin coating at 2000 rpm, baked at 150° C. for one minute. Thereafter the wafer was maintained at 350–400° C. for 3 hours in a nitrogen atmosphere to determine thickness decreasing rates per one hour of the film. The results are shown in TABLE 2.

TABLE 2

| Example | Heat treatment temperature | Amount of decrease in thickness |
|---|---|---|
| 12 | 350° C. | <0.1%/Hr |
| 13 | 375° C. | <0.1%/Hr |
| 14 | 400° C. | 1.2%/Hr |

Examples 15–17

The wafers coated in EXAMPLES 9–11 were each immersed in ultrapure water at room temperature and allowed to stand therein for five hours. Each of the wafers was removed from ultrapure water, spin-dried and then baked at 150° C. for one minute. The film coating each wafer was measured as to its relative dielectric constant in the same manner as in EXAMPLES 9–11. As seen from TABLE 3, any rise in dielectric constant due to absorption of water in particular was not noticed. Further, it was confirmed by FT-IR analysis that there was found no water absorption peak within the range between 3000 cm$^{-1}$ and 3300 cm$^{-1}$.

TABLE 3

| Example | Wafer used | Relative dielectric constant after treatment | Occurrence of water absorption peak found by FT-IR analysis |
|---|---|---|---|
| 15 | Example 9 | 2.8 | Not found |
| 16 | Example 10 | 2.8 | Not found |
| 17 | Example 11 | 2.8 | Not found |

Example 18

Resin H is dissolved in anisole so that the resulting solution has a solid content of 15%. Further, a foaming agent is added to the solution so that the resulting foamed material produced after a heat treatment at 400° C. has a porosity of 20%. The solution is treated in the same manner as in EXAMPLE 9 to for a porous polyether film over a wafer. The relative dielectric constant of this polyether film can be lowered to 2.6.

According to the present invention, it is possible to provide a heat-resistant polyether having a superior heat resistance, satisfactory solubility in organic solvents, low water absorption, and high adhesion to substrates.

What is claimed is:

1. A heat-resistant polyether comprising a repeating unit represented by the formula (1) and having a polystyrene-converted weight-average molecular weight determined by GPC of from 1000 to 50000:

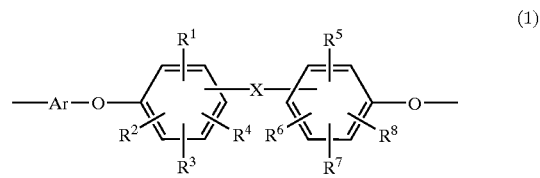

(1)

wherein Ar represents a bivalent organic group having an aromatic ring; $R^1$ to $R^8$ each independently represent a hydrogen atom or an aryl group which may be substituted;

X represents a direct bond or a hydrocarbon group having 1 to 20 carbon atoms, wherein at least one of $R^1$ to $R^8$ is one selected from the following group (C) consisting of aryl groups:

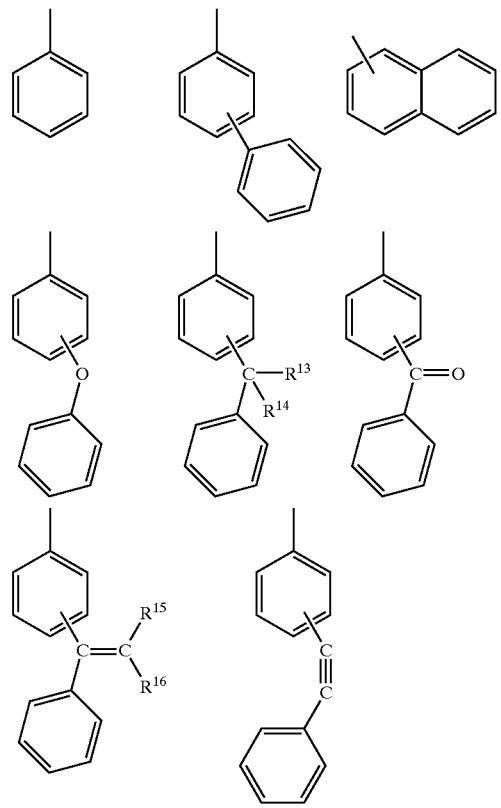

(C)

wherein $R^{13}$ to $R^{16}$ each independently represent an alkyl group having 1 to 3 carbon atoms.

2. The heat-resistant polyether according to claim 1, wherein Ar is one selected from the following group (A) consisting of bivalent organic groups:

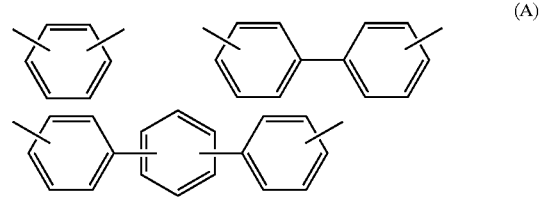

(A)

-continued

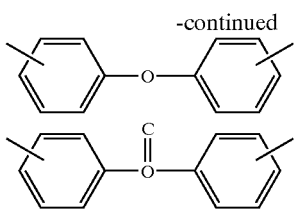

3. The heat-resistant polyether according to claim 1 or 2, wherein the hydrocarbon group having 1 to 20 carbon atoms as X is one selected from the following group (B) consisting of bivalent organic groups:

(B)

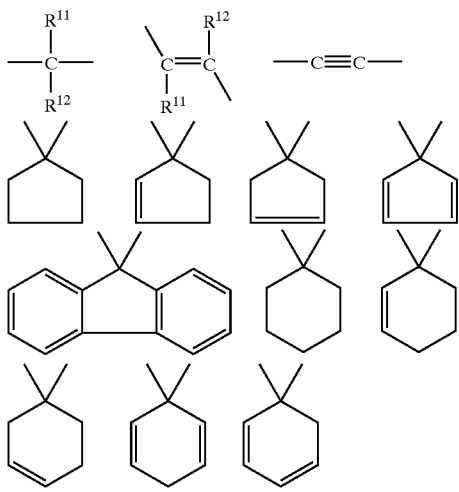

wherein $R^{11}$ and $R^{12}$ each represent an aryl group which may be substituted.

4. The heat-resistant polyether according to claim 1, wherein at least one of $R^1$ to $R^8$ in the formula (1) is a phenyl group.

5. A curable polyether comprising a heat-resistant polyether as recited in claim 1, the heat-resistant polyether further having a functional group capable of crosslinking reaction.

6. The curable polyether according to claim 5, wherein the functional group capable of causing a crosslinking reaction to occur under heating is one selected from the following group (D) consisting of functional groups:

(D)

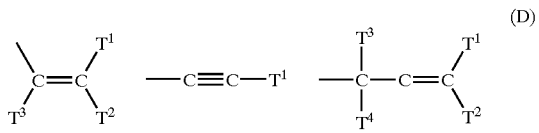

-continued

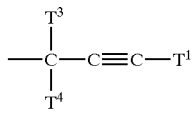

wherein $T^1$ and $T^2$ each represent a hydrogen atom, an alkyl group having 1 to 3 carbon atoms, or an aryl group which may be substituted; and $T^3$ and $T^4$ each represent an alkyl group having 1 to 3 carbon atoms or an aryl group which may be substituted.

7. The curable polyether according to claim 5, wherein the functional group capable of causing a crosslinking reaction to occur under heating is a functional group represented by the formula (3):

(3)

wherein $T^5$ represents an alkenyl group having 2 or 3 carbon atoms or an alkynyl group having 2 or 3 carbon atoms; $T^6$ represents an alkyl group having 1 to 3 carbon atoms or an aryl group which may be substituted; n is 1, 2 or 3; and when n is 2 or 3, $T^5$'s are the same or different, while when n is 1, $T^6$'s are the same or different.

8. The curable polyether according to claim 7, wherein $T^5$ and $T^6$ are each a vinyl group.

9. The curable polyether according to claim 5, which has a crosslinked structure.

10. A heat-resistant polyether film comprising a heat-resistant polyether as recited in claim 1.

11. A curable polyether film comprising a curable polyether as recited in claim 5.

12. A coating liquid for forming a polyether film, comprising a heat-resistant polyether as recited in claim 1, and an organic solvent.

13. A coating liquid for forming a polyether film, comprising a curable polyether as recited in claim 5, and an organic solvent.

14. An insulating film obtained from a coating liquid for forming a polyether film as recited in claim 11.

15. An insulating film obtained from a coating liquid for forming a polyether film as recited in claim 12.

16. An electronic device comprising an insulating film as recited in claim 13 or 14.

* * * * *